United States Patent [19]

Jorgensen et al.

[11] Patent Number: 5,011,285
[45] Date of Patent: Apr. 30, 1991

[54] METHOD AND APARATUS FOR PERFORMING AUTOMATIC PARTICLE ANALYSIS

[75] Inventors: Terje Jorgensen, Skien; Oddbjorn E. Strand, Eidanger; Odd A. Asbjornsen, Arnold, all of Norway

[73] Assignee: Norsk Hydro a.s., Oslo, Norway

[21] Appl. No.: 399,479

[22] PCT Filed: Dec. 16, 1988

[86] PCT No.: PCT/NO88/00095

§ 371 Date: Sep. 20, 1989

§ 102(e) Date: Sep. 20, 1989

[87] PCT Pub. No.: WO89/05971

PCT Pub. Date: Jun. 29, 1989

[30] Foreign Application Priority Data

Dec. 18, 1987 [NO] Norway .................. 875304

[51] Int. Cl.$^5$ .................. G01N 15/02
[52] U.S. Cl. .................. 356/335; 356/336; 250/222.2; 73/DIG. 1
[58] Field of Search .................. 356/335-343, 356/244, 246; 250/222.2, ; 73/DIG. 1, 864.91, 864.82, 864.83

[56] References Cited

U.S. PATENT DOCUMENTS

| | | |
|---|---|---|
| 4,288,162 | 9/1981 | Sakamoto et al. .................. 356/335 |
| 4,295,200 | 10/1981 | Johnson .................. 356/335 |
| 4,497,576 | 2/1985 | Caussignac et al. .................. 356/355 |

FOREIGN PATENT DOCUMENTS

| | | | |
|---|---|---|---|
| 0265139 | 11/1988 | Japan | .................. 356/335 |
| 0016432 | 1/1990 | Japan | .................. 356/335 |

Primary Examiner—Richard A. Rosenberger
Assistant Examiner—Hoa Q. Pham
Attorney, Agent, or Firm—Wenderoth, Lind & Ponack

[57] ABSTRACT

The invention relates to a method and apparatus for automatic analysis for determining the size distribution of particles and their deviation from a desired shape and color. The method includes the collection of particle samples and the generation of a particle curtain in a monolayer form. It is formed by taking particles through a silo whose distance (a) to a vibrating plate positioned below has a length relative to the distance (b) between the outer edge of the plate and the center line of the silo that is large enough for the particles flowing out of the silo and down onto the plate and out over its edge to form an angle α with the horizontal plane. The angle α is 50-90% of the sliding angle of the particulate material. The particle curtain is lit up and the silhouette of the particles therein is recorded and analyzed and presented in at least one place. The apparatus includes a sampler and a silo with at least one level sensor to record the level of particles in the silo and to give a signal to the sampler. The silo has a vertically displaceable extension at its outlet opening. The lower part of the extension is at a distance from a vibrating plate.

11 Claims, 2 Drawing Sheets

METHOD AND APARATUS FOR PERFORMING AUTOMATIC PARTICLE ANALYSIS

BACKGROUND OF THE INVENTION (1) Field of the Invention

The present invention relates to a method for performing an automatic analysis to determine a particle size distribution and deviation from the desired shape and color. The method includes the collection of particle samples and the generation of a particle curtain in a monolayer form, lighting of the latter and taking pictures that are then analyzed. The invention also relates to an apparatus, a particle feeding system, for carrying out the method. This includes means for generating a particle curtain in a monolayer form.

(2) State of the Prior Art

During production of particulate material, or in processes where such material is added in at least one process stage, it is important to be able to control the process, so that the desired size distribution of the particle shaped material is obtained. However, the shape of the particles can also be important for the quality of the product, and therefore it is desirable to know the deviation of the particles from the desired shape and color, so that the process can be controlled with regard to this criteria also.

It has long been desired in the fertilizer industry to have reliable information about the end product size distribution and particle shape, as optimal values for these parameters is of importance both from a purely economical point of view and when using the product, e.g. when spreading the produced prills or granules. Furthermore, a process will be most economical if it gives a product with a narrow sieve span, without having to sieve away large fractions that have to be run in return.

Several analysis apparatus and measuring techniques are already available, and are used to solve the aforesaid problem, however, their applicability is usually limited to very special processes. Thus a particle analysis apparatus is known from U.S. Pat. No. 4,497,576, where a silhouette projection method is used. The apparatus also includes use of parallel laser beams directed through a sample of particles, and means for recording the light which has passed through. This recording is then analyzed to reveal the particle size distribution in the aforesaid sample. A series of conditions which have to be satisfied for the measurements to be representative is listed in the patent, but it doesn't clearly appear how these conditions should be realized. The particles to be analyzed are transported on a conveyor belt and fall from it in front of a light source and down onto the next conveyor belt for return to the process. One condition which is stated is that the particles falling from the conveyor belt must form a monolayer of particles and that they should fall at the same speed. But how such a monolayer is to be practically obtained is not stated, and the aforecited means appears to be badly suited for the application.

Furthermore, from DE number 27 41321, an apparatus for determining the particle size distribution in a falling particle stream by recording and analysis of video pictures is known. The particles flow out of an extended slot in a silo and thereby form a curtain of particles passing a video recorder equipped with a heat picture camera. In addition to the size distribution, the means registers whether the particles deviate strongly form a spherical shape, as the particles' heat content is recorded. The patent neither states how to take representative samples, nor whether special measures are necessary for analyzed particle curtain to be representative. It is stated that fine dust does not substantially disturb the result of the analysis. The apparatus is primarily used for analysis of the size distribution of various additives for asphalt.

Although the aforecited patents give information which clarifies the problem of particle analysis to a certain extent, they do not give practical solutions to the problems of controlling fertilizer granulation/prilling through particle analysis, and that was what the inventor primarily had to find a solution to.

SUMMARY OF THE INVENTION

The object of the present invention was to develop a method and means which could give current information on the deviation of particles from a desired shape, alternatively color or size, to thereby be able to obtain a more even product quality and faster response to operational changes in the process.

The first condition to obtaining good control of a particulation process, for example fertilizer prilling, is that, at any time, representative samples of the intermediate or end product can be taken. The inventors found that the problem could be solved in several ways by adaptations of conventional sampling systems. Accordingly, a container with a slot for a particle inlet may be used. With such a system, samples could be taken by letting the container slot opening traverse the stream of product particles on a conveyor belt or falling from such a belt. The slot opening must pass the whole cross section of the particle stream at regular speed, and fast enough to avoid overfill of the sample container. In addition, it must be possible to completely empty it rapidly so that new samples can be taken. The traversing may, for example, be carried out with the help of double-acting compressed air cylinders.

The next step in the analyzing process was to make the samples accessible for representative analysis, which preferably get analyzed and presented shortly after the sample was taken. The solution to this problem will, to a certain extent, depend on the technique chosen to analyze the particle sample. Sieving and weighing was found to be too time consuming and unsuited for this application. However, some type of picture representation of the particle curtain seemed interesting. The task was then to supply reproducible and representative particle streams of the sample taken. Whether one chooses lighting of the particles by laser beams, infrared light or taking pictures using a film/video camera or photography, it was found that obtaining a particle stream in the form of a monolayer of particles was essential. The means indicated for this in U.S. Pat. No. 4,497,567 could not be used. It was, among other things, very difficult to dimension the conveyor belt properly and set its speed to make sure that one obtained a monolayer of particles over the whole width of the conveyor belt. This apparatus assumes, in addition, that the particle free fall speed is known.

The inventors chose then to feed the particles on to a vibrating plate to generate a monolayer of falling particles. The results of the first tests were so promising that further development of the idea was initiated. It appeared that dosing the particles down on to the plate was a critical parameter. The problem was solved by using a silo whose outlet opening had to be placed in a certain, but adjustable, distance from the plate. Furthermore, the diameter of the outlet opening had to be adapted to the particles to be analyzed. A conventional silo could, for that matter be used, but it appeared to be necessary to provide it with level sensors to measure the distance to the plate and the level of particles in the silo. The last mentioned level sensors could give an impulse to the sampler, for example, so that a more or less constant particle level was maintained in the silo. The distance to the vibrating plate appeared to be critical in obtaining a supply of the correct quantity of particles from the plate. Furthermore, the inventors found that the design of the plate was important to obtaining a regular monolayer of particles supplied from it. A regular monolayer of particles was supplied all around the periphery of the plate adapted to the feed from the silo by choosing a circular plate and adjusting the amplitude and frequency of vibration. An additional parameter appeared under further testing, also to be determined for a good result. The product's angle of inclination against the plate had to be kept below its sliding angle. The sliding angle for the type of product concerned had therefore to be determined, and it was 28° for the tested particle samples. The correct angle may be obtained in different ways or a combination of these. Accordingly, the plate may be given a slightly conical shape, whereby the quantity of particles on the plate is reduced so that the residence time of the particles on the plate is also reduced. Experiments showed that the system functioned very well according to the plans when the angle of inclination of the produce with respect to the horizontal plane was about ⅔ of its sliding angle. A particle feeding system built according to the above stated principles, by adapting the critical parameters to the product's characteristics, particularly the diameter and sliding angle of the particles, was found to be able to deliver a regular flow of particles in a monolayer.

Analysis of the particles in the monolayer could, as already mentioned, be carried out in several ways, but the inventors found it most advantageous to take pictures of the monolayer continuously or discontinuously with, for example, a video camera, so that silhouette pictures of the particles was obtained. Thereby both their shape and size distribution could be registered. Special computer programs for the calculation of the deviation from the desired shape were developed. By measuring the circumference and area of individual particles, their deviation from their desired shape could be calculated and the particle size distribution in the production stream be determined. Generation of the particle curtain and analyzing the particles can be carried out continuously, and the production parameters can be adjusted as a function of the results of the analysis.

BRIEF DESCRIPTION OF THE DRAWINGS

The invention will now be further explained in the following embodiments with reference to the accompanying drawings, in which.

DESCRIPTION OF THE PREFERRED EMBODIMENTS

Figure 1:
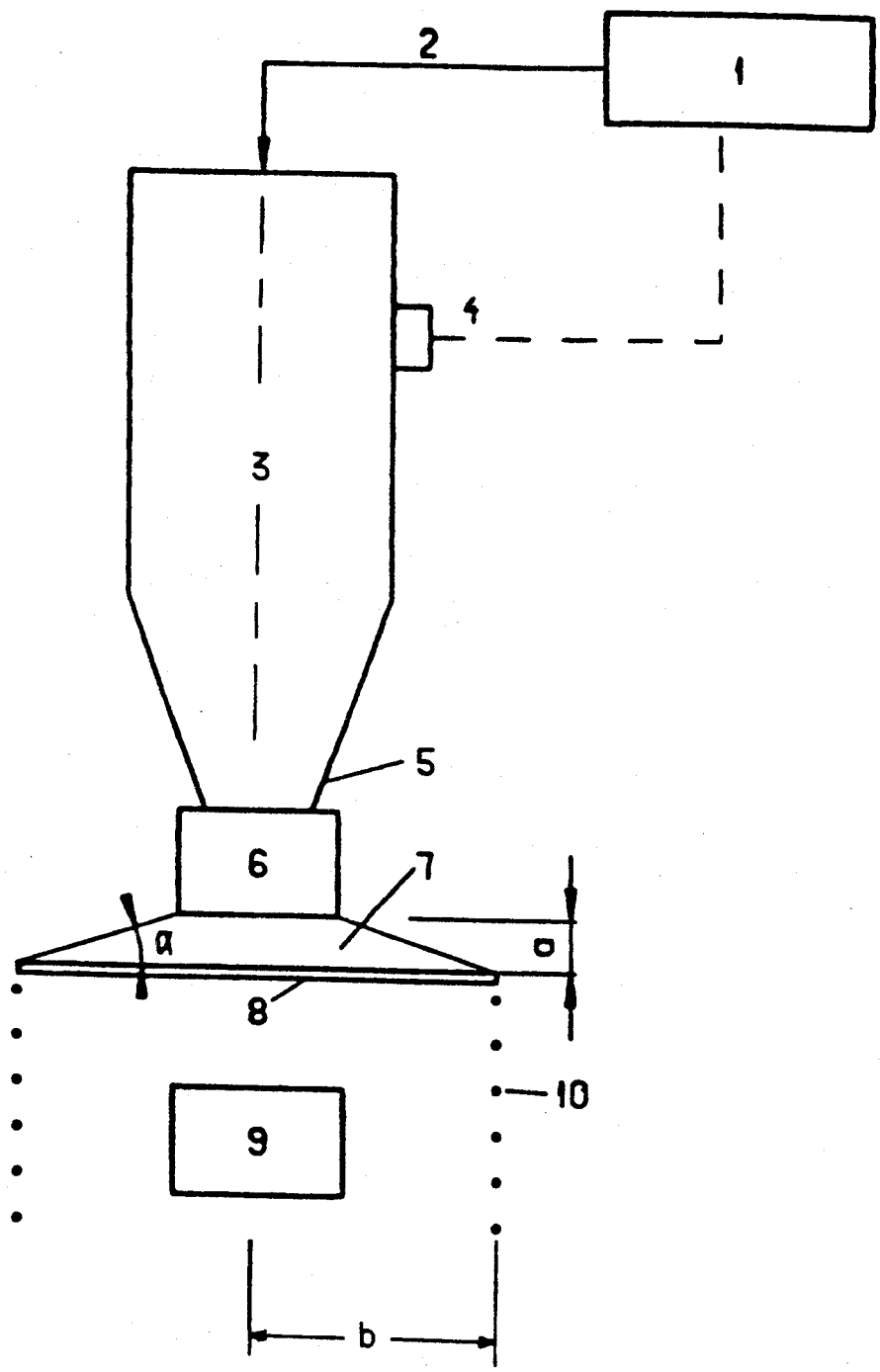
FIG. 1 shows a particle feeding apparatus according to the invention.

A particle feeding apparatus shown in FIG. 1 includes a sampler 1 to collect particle samples at a suitable point in a process, for example a conveyor belt (not shown). The sampler 1 can be a container with a longitudinal slot. When a sample is taken, the sampler 1 is emptied directly into a silo 3, or the sample is sent to the silo via a pipe or a transport device 2. The silo 3 is equipped with a movable extension 6, at the outlet opening of the silo 3. Particles are discharged from the silo 3 down onto a vibrating plate 8, and under operation a layer of particles 7 will, on the plate 8, form an angle α with the horizontal plane. The angle α is smaller than the sliding angle of the product (particles) to be analyzed. It may, for example, be only a few degrees smaller than the sliding angle, but to avoid too sensitive a system, an angle α that is ⅔ of the sliding angle is preferably used. The angle α may be set in several different ways, particularly by regulating and setting the extension 6 at a distance a relative to a distance b from the outer edge of the plate 8 to the center axis of the silo 3, or its cross section, which gives the desired value of the angle α.

The silo 3 may be equipped with a distance sensor 5 to thereby be able to regulate the distance a. Furthermore, silo 3 has at least one level sensor 4. For example, both a minimum and a maximum level in the silo 3 may be registered. Level sensor 4 will give a signal for sampling. Sampling device 1 can accordingly, be connected to a double acting cylinder that, during sampling, lets container 1 traverse the whole width of a particle stream on a conveyor belt or falling from such a belt. Particles will then be caught in the slot in the container, and with the right choice of speed of the container 1 during sampling, it will not be overfilled, and at the same time one is guaranteed a representative sample of the production stream. The silo 3 may also be divided in to several chambers with the help of vertical partitions.

The plate 8 may vibrate in a known manner, and both the frequency and the amplitude may be regulated. By regulating the distance a so that α is smaller than the sliding angle and by vibrating the plate 8, the particles will run out over its edge. Preferably a circular plate 8 is used, and certain sectors of it may be blinded or blocked off so that particles only run out over parts of the periphery of the plate 8. The plate 8 may be made slightly conical, but such that its conicity angle is smaller than the sliding angle. By adjusting the vibration amplitude and/or frequency, one can easily make sure that the particles fall down from the plate in a monolayer 10 of particles. The particle stream or particle curtain 10 may then be lit up by a light source 9. The light source 9 may be a normal lamp, a set of laser beams or a flash which lights at a signal.

Figure 2:
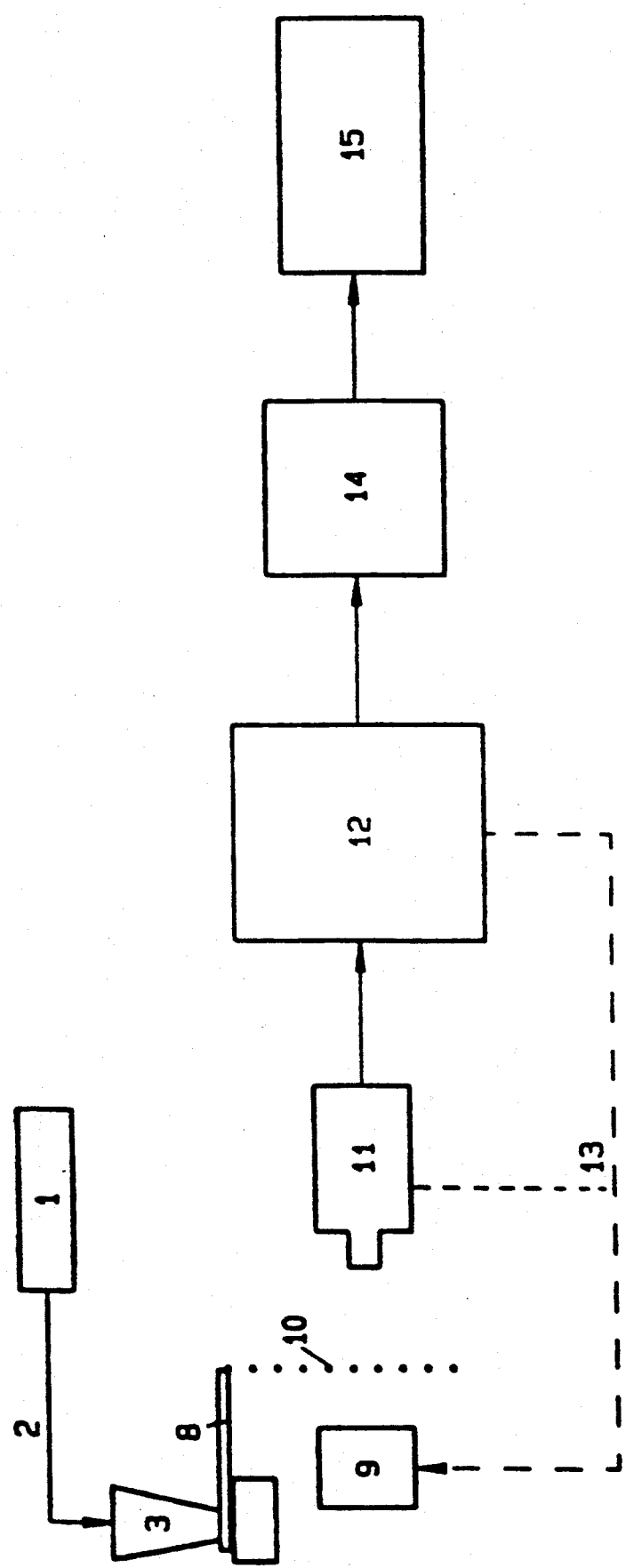
FIG. 2 shows an assembly of units used under the realization of the method according to the invention.

FIG. 2 shows the particle feeding system according to FIG. 1 connected to an apparatus for taking pictures of the particle curtain 10 as well as an apparatus for "on line" analysis and data processing, whereby one gets a complete system for automatic particle analysis.

A unit 11 may be a film or video camera, but also a recording unit for penetrating light, for example laser beams. A video camera taking photographs all the time is preferably used, but if the light source is a flash the photographs will be recorded only at each flash. The unit 12 is a picture analyzer analyzing continuously or discontinuously. This unit can include a signalling arrangement 13 for the release of flash 9 or for picture taking with the unit 11 each time analysis of a picture is completed. The unit 11 may be used to photograph the silhouettes of particles in the particle curtain 10, but may also be used to differentiate between various colors or grey shades of the particles.

The current video picture consists of 512×512 points (picture elements or PIXELS). The number of PIXELS which are black thereby give the area of each particle.

The circumference is determined by a contour following routine. The picture analyzer 12, which may be integrated in a PC, contains the necessary computer programs for reading and storage of pictures to enable measurement of the area and circumference of each particle on the video pictures. The raw data from the picture analyzer 12 is then used for later data processing, for example in a PC 14. With the help of suitable data processing programs, the raw data will be processed so that particle size distribution and various expressions for the deviation of the particles from their desired shape are obtained.

The data from the unit 14 are then presented on at least one unit 15, which may be a printer or computer screen, and the result of the particle analysis is then transferred to the relevant part of the process for controlling the process towards optimal production and product quality. Data may of course also be stored for later study of relevant parts of the process.

EXAMPLE 1

This example illustrates the production of a particle curtain in monolayer form by means of an apparatus according to FIG. 1. Flow characteristics and the sliding angle were first measured for the different types of products. Then each type of product was, one by one, sent through the silo down onto a vibrating, circular plate. The particle level in the silo was kept more or less constant during the tests by supplying new particles, and a silo opening with a size guaranteeing that even the largest particles or particle agglomerates could flow out was used. A circular extension (unit 6 on FIG. 1) was provided around the silo opening, and the extension could be lifted and lowered so as to regulate distance a between the plates and the silo opening.

The distance a was set in such a way that the inclination of the product toward the plane disc roughly ⅔ of the sliding angle of the product. A vibrator was started, whereby the particles started to flow regularly over the periphery of the plate. By varying the vibration frequency and/or amplitude it was made relatively easy to set the vibrator so that the particle curtain consisted of a monolayer of particles. When the right setting for the vibrator was first found, the setting could be kept approximately constant for the same type of product under the whole test. When testing on several types of product, it was found that the inclination angle $\alpha$ for the product should be with respect to the horizontal plane, at least 5% less than its sliding angle, and preferably greater than 50% of its sliding angle, i.e. a range of 50 to 95% of the sliding angle. Adjusting the vibrator to obtain a monolayer was easiest for most types of products when the angle $\alpha$ was between 60 and 70% of the sliding angle of the product.

Vibrator adjustment and/or the extension of unit 6 may, if desired, be controlled with the help of computer programs so that the number of particles in the picture is kept approximately constant.

EXAMPLE 2

This example illustrates automatic particle analysis according to the invention, with results compared to traditional sieving methods (laboratory sieving) of samples as well as deviations from the desired shape.

Calibration was done by placing a completely spherical ball with a known diameter in front of the video camera. The diameter in millimeters was then red into the computer program. The picture analyzer was subsequently tested on completely spherical particles of different sizes. Furthermore, the particles in the individual samples were in advance manually controlled to assess their deviation from spherical shape.

Eight samples of about 2 kg prilled fertilizer were taken. Each sample was laboratory tested to assess particle size distribution and the deviation from the desired shape. The samples were then analyzed according to the invention, the particles being fed with the help of a particle feeding apparatus according to FIG. 1, past a video camera that took pictures of the particles. The analysis shows that pictures which contained 10 to 20 particles took roughly 1 second to analyze. The analysis time could, however, be considerably reduced. As soon as the processing of a picture was finished, a signal was given for a new picture to be taken.

The results of the picture analysis (B) according to the invention, laboratory sieving (L) and deviation from desired shape is given in Table 1, which shows the particle size distribution and the samples of deviations from the desired shape in percentages. The sieving analyses are in gram/100 grams. As it appears from the table, the laboratory sieving covers somewhat wider intervals (sieving categories) than the picture analysis.

TABLE 1

| | PARTICLE ANALYSIS | | | | | | | | | | | | |
|---|---|---|---|---|---|---|---|---|---|---|---|---|---|
| | Deviation % | +4.5 mm % | 4.00 mm % | 3.75 mm % | 3.15 mm % | 2.80 mm % | 2.36 mm % | 2.00 mm % | 1.70 mm % | 1.40 mm % | 1.00 mm % | 0.50 mm % | −0.50 mm % |
| L | 12.3 | 6.2 | | 23.9 | | 17.9 | 25.9 | 13.2 | 9.4 | | 2.2 | 1.1 | 0.3 |
| B | 12.7 | 2.6 | 4.8 | 4.0 | 2.01 | 17.8 | 22.1 | 13.3 | 7.6 | 4.3 | 2.8 | 0.5 | 0.3 |
| L | 10.6 | 5.2 | | 21.4 | | 18.6 | 28.0 | 14.9 | 8.8 | | 2.0 | 0.8 | 0.2 |
| B | 11.4 | 3.6 | 3.6 | 2.5 | 14.3 | 15.8 | 22.4 | 15.8 | 10.1 | 6.7 | 4.2 | 0.9 | 0.1 |
| L | 7.5 | 1.6 | | 20.0 | | 20.5 | 35.6 | 18.9 | 3.2 | | 0.1 | 0 | 0 |
| B | 11.0 | 1.3 | 4.0 | 4.3 | 20.1 | 20.4 | 28.1 | 16.1 | 5.4 | 0.8 | 0.2 | 0 | 0 |
| L | 7.7 | 2.8 | | 16.1 | | 18.4 | 31.9 | 17.4 | 10.5 | | 2.2 | 0.6 | 0.1 |
| B | 9.5 | 1.4 | 3.0 | 2.7 | 15.9 | 18.2 | 26.2 | 15.6 | 8.0 | 4.6 | 2.9 | 0.4 | 0 |
| L | 11.0 | 1.4 | | 20.2 | | 22.4 | 35.9 | 16.9 | 3.1 | | 0.1 | 0 | 0 |
| B | 11.0 | 1.6 | 2.9 | 3.8 | 19.7 | 21.7 | 29.0 | 15.6 | 5.1 | 0.7 | 0.2 | 0 | 0 |
| L | 18.0 | 10.0 | | 28.0 | | 18.7 | 21.9 | 10.0 | 7.2 | | 2.2 | 1.5 | 0.4 |
| B | 18.3 | 5.2 | 6.5 | 6.2 | 22.8 | 18.0 | 17.7 | 10.8 | 5.7 | 3.3 | 2.9 | 0.8 | 0.1 |
| L | 3.9 | 0.6 | | 16.1 | | 17.6 | 34.8 | 21.0 | 9.4 | | 0.5 | 0 | 0 |
| B | 8.4 | 0.3 | 3.0 | 3.0 | 15.8 | 18.0 | 27.7 | 18.3 | 10.4 | 2.8 | 0.8 | 0.1 | 0 |

TABLE 1-continued

| | PARTICLE ANALYSIS | | | | | | | | | | | | |
|---|---|---|---|---|---|---|---|---|---|---|---|---|---|
| Deviation % | +4.5 mm % | 4.00 mm % | 3.75 mm % | 3.15 mm % | 2.80 mm % | 2.36 mm % | 2.00 mm % | 1.70 mm % | 1.40 mm % | 1.00 mm % | 0.50 mm % | −0.50 mm % |
| L | 4.3 | | 1.2 | | 12.8 | | 14.6 | 27.8 | 18.4 | 15.4 | | 5.7 | 3.3 | 0.4 |
| B | 6.0 | 0.8 | 1.5 | 2.2 | 11.8 | 14.0 | 23.8 | 17.4 | 11.6 | 8.1 | 7.2 | 1.6 | 0.1 |

As it appears in Table 1, there is a very good accordance between the results of particle size distribution measured by laboratory sieving and by the method according to the invention. As far as the analysis of the deviation from the spherical shape is concerned, it corresponds well with common judgements concerning good and poor products. However, the method according to invention gave a more accurate expression of the deviation of the particles from their desired shape.

EXAMPLE 3

This example shows an investigation of granulated fertilizer particles. The studies were carried out in the same way as described in Example 1, but in the last example the deviation from the desired shape was only studied by the method according to the invention. The results of this investigation are given in Table 2.

TABLE 2

| | PARTICLE ANALYSIS | | | | | | | | | | | | |
|---|---|---|---|---|---|---|---|---|---|---|---|---|---|
| Deviation % | +4.5 mm % | 4.00 mm % | 3.70 mm % | 3.10 mm % | 2.80 mm % | 2.40 mm % | 2.00 mm % | 1.70 mm % | 1.40 mm % | 1.00 mm % | 0.50 mm % | −0.50 mm % |
| L | — | | 0.1 | | 76.2 | | 23.4 | | | 0.3 | | — | — |
| B | 8.4 | 0.6 | 2.3 | 6.3 | 39.8 | 32.3 | 14.9 | 3.4 | 0.3 | — | — | — | — |
| B | 8.4 | 0.2 | 1.7 | 6.4 | 42.3 | 29.9 | 14.3 | 4.8 | 0.5 | — | — | — | — |
| B | 8.5 | 0.3 | 2.5 | 7.7 | 40.5 | 28.9 | 15.6 | 4.0 | 0.5 | — | — | — | — |
| L | — | | 1.5 | | 83.3 | | 14.9 | | | 0.2 | 0.1 | 0.0 | 0.1 |
| B | 41.8 | 1.8 | 7.8 | 12.9 | 41.7 | 26.9 | 7.6 | 1.0 | 0.2 | — | — | — | — |
| B | 39.8 | 1.3 | 9.8 | 10.5 | 41.5 | 26.5 | 9.6 | 0.6 | 0.1 | 0 | 0 | 0.1 | 0 |
| B | 40.2 | 1.0 | 7.1 | 12.9 | 47.3 | 23.5 | 7.0 | 0.8 | 0.1 | 0.1 | — | — | — |
| L | — | | 0.9 | | 47.1 | | 49.2 | | | 2.6 | | 0.1 | 0.1 |
| B | 24.6 | 1.7 | 7.4 | 7.6 | 22.2 | 16.8 | 23.3 | 17.9 | 2.9 | 0.2 | — | — | — |
| B | 30.4 | 1.6 | 6.7 | 6.3 | 23.8 | 14.4 | 25.6 | 18.5 | 2.4 | 0.2 | 0 | 0.1 | — |
| B | 27.3 | 1.7 | 7.7 | 7.0 | 20.9 | 19.1 | 23.6 | 17.2 | 2.4 | 0.2 | 0.1 | — | — |
| L | — | | 0.2 | | 40.4 | | 52.1 | | | 7.1 | | 0.1 | 0.1 |
| B | 44.0 | 0.6 | 3.8 | 4.6 | 18.7 | 20.3 | 28.7 | 17.7 | 4.5 | 0.8 | 0.2 | 0.1 | — |
| B | 42.6 | 1.1 | 3.8 | 3.7 | 19.5 | 18.9 | 28.0 | 19.7 | 4.8 | 0.7 | 0.1 | 0.2 | — |
| B | 43.4 | 0.7 | 2.1 | 3.7 | 22.8 | 21.8 | 21.8 | 17.8 | 5.0 | 0.9 | 0.2 | 0.3 | — |

There is also, for the granulated product, a good accordance between the two methods of analysis as far as particle size distribution is concerned. Analysis of the deviation of the particles from the desired shape gave, for this type of product too, a good accordance with the real conditions.

When the particle feed system was connected to a prilling process such that samples were taken from the flow of product, it took, all in all, less than 5 minutes from the change of operating conditions in the relevant part of the process until it was recorded on the particle analyzer. Compared to conventional methods of analysis, this is more than fast enough for most particulating processes.

It is, however, possible to reduce the total time of analysis, and hence the response time, too, without this influencing the quality of the analysis of the accuracy.

Tests have shown that the automatic particle analyzer is well suited for particles in the measurement range of 0.5 to 10.0 mm, but with small physical changes it is fully possible to displace this measurement range considerably. Furthermore, it has been shown that dust in the particle samples gives no problems.

A special application which was carried out on order was an analysis of particles with different colors/shades of grey. During testing it appeared that one, for example, could determine the number of black and light particles in a sample. This was achieved by applying a contrast plate or device during photographing of the particle curtain. At the same time, analysis of particle size distribution could be carried out.

Through the present invention one has achieved a particle feeding means which in a consistent and practical form can transfer a particle sample to a particle curtain in the form of a monolayer of particles that is representative for the particle distribution in the sample/product stream. By means of this arrangement representative samples of one or several product streams can quickly be taken and transferred to a monolayer that can be analyzed, particularly with respect to particle size distribution and deviation from the desired shape.

When analyzing the particles one found it particularly advantageous to light these by means of a flash that is automatically triggered as soon as a picture has been completely treated. For each flash, a photograph of the particles is then taken. This gave a very accurate and quick analysis of the particle curtain.

The method and the apparatus according to the invention may be applied to all known particulating processes and processes where addition of particles with the desired size distribution and shape is important. But the invention will be applicable for verification of finished particulated product too. Such applications may be: analysis during bulk loading, packing in bags or the like, or verification of the specifications of particulate products. The particle analyzer according to the invention may also be applied when analyzing small samples of laboratories.

We claim:

1. A method of automatically analyzing a sample group of particles to determine the size distribution of the particles and their deviation from a desired shape, comprising the steps of:

providing a container for particle samples, said container having an outlet for the particles, a vibrating plate having an outer edge positioned below said outlet a distance a, wherein the length between a center line of said outlet of said container and said outer edge of said vibrating plate is a distance b, said distances a and b being chosen such that the particles of the particle samples will flow from said outlet of said container onto said vibrating plate and over said outer edge in a monolayer when said plate vibrates, with an angle $\alpha$ of the surface of the particles on said vibrating plate relative to a horizontal plane at 50% to 90% of the sliding angle of the particles;

placing particle samples in said container such that the particle samples flow through said container and onto said vibrating plate via said outlet;

vibrating said vibrating plate with the particle samples thereon so as to form a monolayer of said particles flowing over said outer edge of said vibrating plate;

lighting said monolayer;

pictorially recording said monolayer while said monolayer is lit to obtain a pictorial record of said monolayer; and analyzing said pictorial record of said monolayer to determine the size distribution of the particles therein.

2. The method as set forth in claim 1, wherein:

said step of pictorally recording said pictorial record comprises, when particles of different shades of color are to be analyzed, contrasting some of the particles by applying a contrast device having a shade of color the same as a shade of color of other particles so as to exclude the other particles from analysis.

3. The method as set forth in claim 1, and further comprising the steps of:

providing a sampler;

collecting samples of particles from a stream of particles with said samples; and feeding the samples of particles to said container;

wherein said step of providing a container further comprises providing at least one level sensor for detecting the level of particles in said container and signalling said sampler for the collection of samples of particles.

4. The method as set forth in claim 1, and further comprising the steps of:

providing a sampler;

collecting samples of particles from a stream of particles with said samples; and feeding the samples of particles to said container;

wherein said step of providing a container further comprises providing at least one level sensor for detecting the level of particles in said container and signalling said sampler for the collection of samples of particles.

5. The method as set forth in claim 1, wherein:

said step of providing a container having an outlet for the particles comprises providing a vertically displaceable extension on said container, said extension forming said outlet.

6. The method as set forth in claim 1, wherein:

said step of providing said vibrating plate comprises providing said vibrating plate such that said outer edge is circular and such that said vibrating plate has a conicity less than said angle $\alpha$.

7. An analyzer for automatically analyzing samples of particles to determine their size distribution and deviation from a desired shape, comprising:

a container for particle samples, said container having a bottom outlet for the particles;

a vibrating plate having an outer edge positioned below said outlet a distance a, wherein the length between a center line of said container and said outer edge of said vibrating plate is a distance b, said distances a and b chosen such that the particles of the particle samples will flow from said outlet of said container onto said vibrating plate and over said outer edge in a monolayer when said vibrating plate vibrates and such that the angle $\alpha$ of the surface of the particle on said vibrating plate is at 50% to 90% of the sliding angle of the particles;

means for lighting the particles flowing over said outer edge of said vibrating plate in the monolayer;

means for pictorially recording the image of the particles in the monolayer when the particles in the monolayer are lit; and means for analyzing the pictorially recorded image of the particles in the monolayer to determine the size distribution of the particles therein and their deviation from a desired shape.

8. The analyzer as set forth in claim 7, wherein:

said means for pictorally recording comprises a contrasting device for, when particles of different shades of color are to be analyzed, contrasting some of the particles by applying said contrasting device, said contrast device having a shade of color the same as a shade of color of other particles so as to exclude the other particles from analysis.

9. The analyzer as set forth in claim 7, and further comprising:

sampling means for collecting samples of particles from a stream of particles and feeding the samples of particles to said container; and at least one level sensing means for detecting the level of particles in the container and signalling the sampler to collect the samples of particles.

10. The analyzer as set forth in claim 7, wherein:

said outlet comprises a vertical displaceable extension on said container, whereby said distance a is adjustable.

11. The analyzer as set forth in claim 7, wherein:

said outer edge of said vibrating plate is circular, and said vibrating plate has a conicity less than said angle $\alpha$.

* * * * *